(12) United States Patent
Ontumi et al.

(10) Patent No.: US 9,770,402 B2
(45) Date of Patent: Sep. 26, 2017

(54) ORAL CARE COMPOSITIONS

(71) Applicant: Colgate-Palmolive Company, New York, NY (US)

(72) Inventors: Dennis Ontumi, Easton, PA (US); Venda P. Maloney, Piscataway, NJ (US); Suman K. Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/101,124

(22) PCT Filed: Dec. 2, 2013

(86) PCT No.: PCT/US2013/072679
§ 371 (c)(1),
(2) Date: Jun. 2, 2016

(87) PCT Pub. No.: WO2015/084315
PCT Pub. Date: Jun. 11, 2015

(65) Prior Publication Data
US 2016/0303030 A1    Oct. 20, 2016

(51) Int. Cl.
*A61K 8/891* (2006.01)
*A61K 8/34* (2006.01)
*A61K 8/37* (2006.01)
*A61Q 11/00* (2006.01)

(52) U.S. Cl.
CPC ............... *A61K 8/891* (2013.01); *A61K 8/34* (2013.01); *A61K 8/37* (2013.01); *A61Q 11/00* (2013.01); *A61K 2800/40* (2013.01)

(58) Field of Classification Search
CPC .................................................... A61G 11/00
See application file for complete search history.

(56) References Cited

U.S. PATENT DOCUMENTS

| 6,123,950 | A | 9/2000 | Hughes |
| 6,303,268 | B1 * | 10/2001 | Namba ............... C08G 77/442 430/270.1 |
| 6,569,408 | B1 | 5/2003 | Yue et al. |
| 6,589,512 | B1 * | 7/2003 | Yue ..................... A61K 8/0208 424/49 |
| 7,118,732 | B2 | 10/2006 | Ibrahim et al. |
| 2001/0007652 | A1 | 7/2001 | Takeda et al. |
| 2005/0038135 | A1 | 2/2005 | Jin et al. |
| 2006/0111465 | A1 | 5/2006 | Jia et al. |
| 2006/0142411 | A1 | 6/2006 | Ibrahim et al. |
| 2007/0166271 | A1 * | 7/2007 | Gordon ................. A61K 8/585 424/70.122 |
| 2008/0305062 | A1 * | 12/2008 | Bui ......................... A61Q 1/04 424/64 |
| 2010/0081837 | A1 * | 4/2010 | Saito .................... C08G 77/045 556/413 |
| 2011/0020413 | A1 | 1/2011 | Gormley et al. |
| 2013/0004446 | A1 | 1/2013 | Bui et al. |
| 2013/0266523 | A1 | 10/2013 | Gu et al. |
| 2014/0308321 | A1 * | 10/2014 | Midha .................... A61K 8/891 424/401 |

FOREIGN PATENT DOCUMENTS

| EP | 0528457 | 2/1993 |
| GB | 686429 | 1/1953 |
| JP | 2012-116768 | 6/2012 |
| WO | WO 02/34221 | 5/2002 |

OTHER PUBLICATIONS

"Investigation of the Structure of Polymerizable Silsesquioxanes by GPC and MALDI-TOF-MS in Relation to their Viscosity" authored by Klapdohr et al. and published in Monatshefte für Chemie (2006) 137, 667-679.*
International Search Report and Written Opinion in International Application No. PCT/US2013/072679, mailed Jul. 14, 2014.

* cited by examiner

*Primary Examiner* — Marc Zimmer

(57) ABSTRACT

Described herein are oral care compositions comprising a silsesquioxane silicone resin and a solvent; and methods of making and using the same.

24 Claims, No Drawings

ORAL CARE COMPOSITIONS

BACKGROUND

Consumers desire whiter and shinier teeth faster, so there is a growing need to provide consumers with products that can offer instant whitening and teeth shine. However, it is difficult to provide a glossing product that dries upon contact with the moist tooth surface of the enamel in order to make the enamel shinier. Most whitening products work by providing gradual improvements to the whiteness of a tooth surface. The most effective whitening products use hydrogen peroxide to oxidise enamel stains. Such products do not however make the enamel surface glossier.

It would therefore be desirable to provide an oral care composition that can form an improved, enamel shine coating and improve overall enamel shine.

SUMMARY

A first aspect of the present invention provides an oral care composition comprising
(i) a silsesquioxane silicone resin and
(ii) a solvent.

Optionally the silicone resin comprises at least 50 mole % trifunctional units of formula $RSiO_{3/2}$ wherein R is the same or different and is selected from hydrogen, $C_1$ to $C_4$ alkyl, aryl and phenyl. Further optionally the silicone resin comprises front 50 mole % to 100 mole % trifunctional units of formula $RSiO_{3/2}$ wherein R is the same or different and is selected from hydrogen, $C_1$ to $C_4$ alkyl, aryl and phenyl. Further optionally the silicone resin comprises from 60 mole % to 99 mole % trifunctional units of formula $RSiO_{3/2}$ wherein R is the same or different and is selected from hydrogen, $C_1$ to $C_4$ alkyl, aryl and phenyl. Further optionally, 60 mole % to 100 mole % R is methyl.

Optionally the silsesquioxane silicone resin is polymethylsilsesquioxane.

Optionally the solvent comprises one or more of ethanol, ethyl acetate, and mixtures thereof. Further optionally the solvent comprises ethanol. Even further optionally the solvent consists of ethanol. The solvent may be diluted further with a humectant, such as glycerine, polyethylene glycol, or polypropylene glycol.

Optionally the composition comprises from 20 to 99 weight % silsesquioxane silicone resin. Further optionally the composition comprises from 30 to 90 weight % silsesquioxane silicone resin. Even further optionally the composition comprises from 60 to 80 weight % silsesquioxane silicone resin. Even further optionally the composition comprises from 65 to 75 weight % silsesquioxane silicone resin. Further optionally the composition comprises 70 weight % silsesquioxane silicone resin.

Optionally the composition comprises 10 to 50 weight % solvent. Further optionally the composition comprises 20 to 40 weight % solvent. Even further optionally the composition comprises 40 weight % solvent.

Optionally the composition comprises 60 to 80 weight % silsesquioxane silicone resin and 20 to 40 weight % solvent. Further optionally the composition comprises 70 weight % silsesquioxane silicone resin and 30 weight % solvent.

Optionally the composition comprises less than 3 weight % water. Further optionally the composition comprises less than 1 weight % water. Even further optionally the composition comprises from 0 to 1 weight % water.

Optionally the oral care composition is a paint-on composition, tooth varnish, sealant or coating.

Optionally the oral care composition further comprises an oral care active selected from one or more of a fluoride ion source, an antisensitivity agent, a tooth whitening agent, e.g., blue pigment or dye, a tooth bleaching agent, e.g., hydrogen peroxide or polyvinyl pyrrolidone-hydrogen peroxide, an antibacterial agent, an anti-calculus agent and mixtures thereof.

Optionally the oral care composition further comprises a flavour agent.

According to a further embodiment, the invention provides a method of treating a tooth comprising applying a composition to a surface of a tooth.

According to a yet further embodiment, the invention provides a method of tooth glossing comprising applying a composition to a surface of a tooth.

According to a yet further embodiment, the invention provides use of a composition to enhance the gloss of a surface of a tooth.

According to a yet further embodiment, the invention provides a composition for use in a method of treating a tooth or a method of tooth glossing, said method comprising applying said composition to a surface of said tooth.

DETAILED DESCRIPTION

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In order to provide shine benefit to tooth enamel including human tooth enamel, difficulties associated with coating the saliva coated enamel surface must be overcome. A fast drying time upon contact with the wet tooth surface is critical to obtaining a uniform and consistent film layer on the tooth surface. It has now surprisingly been found that combining a solvent (which has a low drying time) with a silsesquioxane silicone resin (which is capable of adhering to a tooth surface) results in an oral care composition which can provide a film that results in a visibly shinier enamel surface. The compositions of the present invention result in a glossier enamel surface when compared to enamel surfaces treated with a shellac-containing formula. Gloss is a measure of the proportion of light that has specular reflection from a surface. Gloss can be measured visually comparing pre and post-treatment glossiness, for example, using photographic images. Optionally, gloss can also be measured relative to a black glass standard with a defined refractive index. Such a standard is given a gloss value of 100 gloss units (GU) and a scale is created in which 0 GU is a perfectly matte surface. Typically, a surface can be considered to be high gloss if it possesses a gloss of great than 70 GU at 60°. For example, a glossy surface may have a gloss of 70 to 2000 GU, 70 to 1000 GU, 70 to 500 GU, 70 to 250 GU or 70 to 100 GU. The gloss of high gloss surfaces may be measured at angles other than 60°, for example 20° or 80°.

Siloxane polymers are cross-linked polymers that have a basic backbone of silicon and oxygen with side constituent groups that may be the same or different and can generally be described by the structural repeating unit (—O—

SiRR'—)$_n$ where R and R' may be the same or different side constituent groups and n may be any value above 2 designating the repetition of the structural repeating unit (SRU) in the polymer backbone. Siloxane polymers are also known as "silicone" polymers. Siloxane polymers may include poly-heterosiloxanes where side groups and/or structural repeating units may be different entities (having different side constituent groups), such as, for example, the siloxane co-polymer described by the nominal SRU formula (—O—SiRR')$_n$—(—O—Si—R"R"')$_m$ wherein R and R' are side groups distinct from R" and R"'. Further R and R' may be different from one another, likewise the same may be true for R" and R"'. Such siloxane polymers may terminate in any variety of terminal groups, such as for example, trimethyl silyl ((CH$_3$)$_3$Si terminated siloxane.

Silicone resins can be highly crosslinked polymeric siloxane systems. The crosslinking is introduced through the incorporation of tri-functional and tetra-functional silanes with mono-functional or di-functional (or both) silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence a sufficient level of crosslinking) such that they dry down to a rigid or hard film are considered to be silicone resins. The ratio of oxygen atoms to silicon atoms is indicative of the level of crosslinking in a particular silicone material. Silicone resins generally have at least 1:1 oxygen atom per silicon atom. Typical silanes used in the manufacture of silicone resins are the monomethyl, dimethyl, monophenyl, diphenyl, methylphenyl, monovinyl and methylvinyl-chlorosilanes and tetrachlorosilanes. In particular, methyl, ethyl or phenyl substituted silicone resins are used.

Silicone resins can be identified according to the "MDTQ" nomenclature where the silicone resin is described according to the presence of various siloxane monomer units. The symbol M denotes the mono-functional unit ((CH$_3$)$_3$Si)$_{1/2}$ having only one available oxygen for binding. At least one of the methyl groups of the M unit may be replaced by another group, for example to give a unit with formula [R(CH$_3$)$_2$]SiO$_{1/2}$ wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups and ether groups wherein the groups other than methyl groups may be further substituted. The M units are generally used for end blocking or terminal groups. D denotes the di-functional unit (CH$_3$)$_2$SiO having, two available oxygen groups. Again, at least one of the methyl groups of the D unit may be replaced by another group, for example to give a unit with formula R$_a$R$_b$SiO, RCH$_3$SiO or wherein R$_a$ and R$_b$ may be chosen from groups other than methyl groups. Non-limiting examples of such groups other than methyl groups include alkyl groups other than methyl groups, alkene groups, alkyne groups, hydroxyl groups, thiol groups, ester groups, acid groups and ether groups wherein the groups other than methyl groups may be further substituted. The D units are generally used as chain extenders. The T denotes the tri-functional unit CH$_3$SiO$_{3/2}$ having three available oxygens for binding. The methyl group may be replaced by another group, for example to give a writ with formula RSiO$_{3/2}$, wherein R may be chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, phenyl groups and alkoxy groups wherein the groups other than methyl groups may be further substituted. The T units are generally used to design silicone resins which are cage shaped or three dimensional. Q denotes the quadra- or tetra-functional unit having four available oxygen groups. As already outlined above, the MDTQ standard substituent methyl may be substituted for other groups. Such alternative substituents may include vinyl, phenyl, amino, hydroxyl etc. substituents. The differences in substituent groups are denoted using primes (e.g. M'). The inclusion of these alternate substituent groups may increase the resin compatibility with other organic materials. The description of the silicone resin is complete with the notation of any non-methyl substituent groups and molar ratios of the various units, either in terms of subscripts to the symbols indicating the total number of each type of unit in the silicone, or an average thereof, or as specifically indicated ratios in combination with molecular weight.

Silsesquioxane resins are a specific form of silicone resins, made up predominantly of trifunctional units or T units. It is preferred that the silsesquioxane resin of the present invention is a polyorganosilsesquioxane. Polyorganosilsesquioxanes are polymers of the empirical formula [RSiO$_{3/2}$]$_n$, made by condensing silanes of the empirical formula RSi(R')$_3$, where R is generally H, substituted or unsubstituted C$_1$ to C$_4$ lower alkyl group or aryl group including phenyl; R' is —Cl or —OR. This class of polymers can form several distinct morphological structures depending on the reaction conditions and variable radicals employed. For instance, a sheet-like coating resin is useful in electronic coatings when R is H. When R is methyl, mono-dispersed spherical micronized particles can be created.

The silsesquioxane may be a resin of general formula R$_n$SiO$_{(4-n)/2}$ wherein R is independently chosen from a hydrogen atom and a monovalent hydrocarbon group comprising 1 or 3 carbon atoms, wherein more than 80 mole % of R are methyl or propyl groups, n is a value from 1.0 to 1.4, more than 60 mole % of the copolymer comprises RSiO$_{3/2}$ units and having a hydroxyl or alkoxy content from 0.2 to 10% by weight, for example between 1 and 4% by weight, preferably between 5 and 10% by weight and more preferably between 6 and 8% by weight.

In addition to T units of formula CH$_3$SiO$_{3/2}$ polyorganosilsesquioxanes may also contain D units of formula (CH$_3$)$_2$SiO.

The silicone resin preferably comprises at least 50 mole % trifunctional units of formula RSiO$_{3/2}$ wherein R is the same or different and is selected from hydrogen, C$_1$ to C$_4$ alkyl, aryl and phenyl. In one embodiment, the silicone resin comprises from 50 mole % to 100 mole % trifunctional units of formula RSiO$_{3/2}$ wherein R is the same or different and is selected from hydrogen, C$_1$ to C$_4$ alkyl, aryl and phenyl. For example, the silicone resin may comprise from 60 mole % to 100 mole %, from 60 mole % to 99 mole % from 65 mole % to 99 mole %, or from 75 mole % to 99 mole % trifunctional units of formula RSiO$_{3/2}$ wherein R is the same or different and is selected from hydrogen, C$_1$ to C$_4$ alkyl, aryl and phenyl.

The R group can be the same or different and can be selected from hydrogen, C$_1$ to C$_4$ alkyl, aryl and phenyl. In one embodiment R is predominantly methyl or propyl. Preferably from 60 mole % to 100 mole % R is methyl or propyl, for example 60 mole % to 99 mole %. More preferably R is predominantly methyl, for example from 60 mole % to 100 mole % R is methyl, or from 60 mole % to 99 mole % R is methyl.

In one embodiment the weight average molecular weight of the silsesquioxane silicone resin is from 5000 to 15,000 Daltons. For example, from 6,000 to 14,000 Daltons, from 7,500 Daltons to 12,500, from 8,000 Daltons to 12,000 Daltons or from 9,000 Daltons to 11,000 Daltons. In one embodiment, the silsesquioxane silicone resin has a weight average molecular weight of 10,000 Daltons.

One example of a preferred polymethylsilsesquioxane is Belsil PMS MK (also known as Resin MK) available from Wacker Chemie. One example of a preferred polyphenylsilsesquioxane is Belsil SPR45VP. The silsesquioxane silicone resin may also be a polypropylsilsesquioxane.

In one embodiment the composition comprises from 20 to 99 weight % silsesquioxane silicone resin. For example, the composition may comprise from 40 to 90 weight %, from 45 to 90 weight %, from 45 to 85 weight %, from 50 to 80 weight %, from 55 to 80 weight %, from 60 to 80 weight %, from 55 to 75 weight %, from 60 to 75 weight % or from 65 to 75 weight % silsesquioxane silicone resin. For example, the composition may comprise 70 weight % silsesquioxane silicone resin.

The compositions of the present invention comprise a solvent for the resin. Preferably this solvent has a low drying time. A faster drying time upon contact with the wet tooth surface allows formation of a uniform and consistent film layer on the tooth surface, forming an improved enamel shine coating. In some embodiments, a film can form from the composition as the solvent is removed, for example through evaporation. Preferably, the oral care composition dries upon contact with the wet tooth surface. For example, the oral care composition may have a drying time on the tooth surface of less than 2 minutes, less than 1 minute, less than 30 seconds, less than 20 seconds, less than 10 seconds, less than 5 seconds or less than 2 seconds. For example, the oral care composition may have a drying time of from 0.5 seconds to 2 seconds or from 0.5 seconds to 5 seconds.

Organic solvents for the resin suitable for use in the compositions of the present invention include organic solvents such as alcohols and esters. In one embodiment, the solvent comprises one or more of ethanol, ethyl acetate, and mixtures thereof. A particularly preferred solvent is ethanol. In one embodiment, the solvent consists of ethanol. The solvent may be diluted further with a humectant, such as glycerine, polyethylene glycol, or polypropylene glycol.

In one embodiment the composition comprises from 10 to 50 weight % solvent. In one embodiment the composition comprises from 20 to 50 weight % solvent, from 20 to 45 weight % solvent or from 30 to 45 weight % solvent. For example, the composition may comprise 35 to 42 weight % solvent, especially 40 weight % solvent. In one embodiment the composition comprises from 20 to 50 weight % ethanol, from 20 to 45 weight % ethanol or from 30 to 45 weight % ethanol. For example, the composition may comprise 35 to 42 weight % ethanol, in particular 40 weight % ethanol.

In one embodiment, the oral care composition comprises from 60 to 80 weight % silsesquioxane silicone resin and from 20 to 40 weight % solvent. For example, the composition may comprise from 65 to 75 weight % silsesquioxane silicone resin and from 25 to 35 weight % solvent. In one embodiment, the oral care composition may comprise from 68 to 72 weight % silsesquioxane silicone resin and from 28 to 32 weight % solvent.

In one embodiment the composition comprises less than 3 weight % water, for example from 0 weight % to 3 weight % water, from 0 weight to 2 weight % water or from 0 weight % to 1 weight % water.

In one embodiment the oral care composition is a paint-on composition, tooth varnish, sealant or coating, in one embodiment the oral care composition is applied by brush, for example by dipping a brush into the composition and then applying it to a tooth surface. The composition may remain on the tooth surface temporarily, for example it may wear off the tooth surface within 48 hours of application, within 24 hours of application, within 12 hours of application, within 6 hours of application or within 2 hours of application.

The oral care composition according to claim may further comprise an oral care active. In one embodiment, the oral care composition comprises an oral care active selected from one or more of a fluoride ion source, an antisensitivity agent, an occlusion agent, a tooth whitening agent, a tooth bleaching agent, an antibacterial agent, an anti-calculus agent and mixtures thereof.

Tooth whitening agents suitable for use in the present invention may include, but not limited to, titanium dioxide, zinc oxide, hydroxyapatite mica, titanium dioxide coated mica, and blue pigment or dye. Tooth bleaching agents suitable for use in the present invention may include, but not limited to, hydrogen peroxide and polyvinyl pyrrolidonehydrogen peroxide.

Fluoride sources suitable for use in the present invention may include, but are not limited to: ionic fluorides including alkali metal fluorides; amine fluorides such as olaflur (N'-octadecyltrimethylendiamine-N,N,N'-tris(2-ethanol)-dihydrofluoride), indium fluoride, sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycin hydrofluoride, amine fluoride or combinations thereof; and ionic monofluorophosphates including alkali metal monofluorophosphates such as potassium, sodium and ammonium fluoride and monofluorophosphates and mixtures thereof. In certain embodiments, the oral care composition of the invention may also contain a source of fluoride ions or fluorine-providing ingredient in amounts sufficient to supply 50 to 5000 ppm fluoride ion, from 100 to 1000, from 200 to 500, or 250 ppm fluoride ion. Fluoride ion sources may be added to the compositions of the invention at a level of 0.001 wt. % to 10 wt. %, e.g., from 0.003 wt. % to 5 wt. %, 0.01 wt. % to 1 wt., or 0.05 wt. %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

In a still further embodiment, a composition of the invention comprises at least one flavorant, useful for example to enhance taste of the composition. Any orally acceptable natural or synthetic flavorant can be used, including, without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxarione, α-irisone, propenyl, guaiethol, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from 0.01 wt. % to 5 wt. %, for example, from 0.1 wt. % to 2.5 wt. %, by total weight of the composition.

The composition of the present invention optionally incorporates one or more antisensitivity agents, e.g., potassium salts such as potassium nitrate, potassium bicarbonate, potassium chloride, potassium citrate, and potassium oxalate; capsaicin; engenol; strontium salts; zinc salts; chloride salts and combinations thereof. Such agents may be added in effective amounts, e.g., from 1 wt. % to 20 wt. % by weight based on the total weight of the composition, depending on the agent chosen. The compositions of the present invention may also be used to treat hypersensitivity by blocking dentin tubules when applied to a tooth.

In some embodiments, the composition of the invention further comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In another embodiment, the composition comprises an orally acceptable zinc ion source useful, for example, as an antimicrobial, anticalculus or breath-freshening agent. One or more such sources can be present. Suitable line ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of from 0.05 wt. % to 3 wt. %, for example from 0.1 wt. % to 1 wt. %, by total weight of the composition.

The composition of the present invention may additionally optionally comprise a tartar control (anticalculus) agent as provided below. Tartar control agents among those useful herein include salts of the specified agents, including alkali metal and ammonium salts. The agents include: phosphates and polyphosphates (for example pyrophosphates), polyaminopropanesulfonic acid (AMPS), polyolefin sulfonates, polyolefin phosphates, diphosphonates such azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®. These are optionally and illustratively present from 0.5 weight % to 5 weight %, based on the total weight of the composition.

In some embodiments, the composition of the present invention further comprises a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, L-lysine, methionine, threonine, levocarnitine and L-carnitine), lipotropics (such as choline, inositol, betaine, and linoleic acid), and mixtures thereof.

The compositions of the present invention can be applied to the surface of a tooth, for example by using a brush, finger, spray, or an applicator, e.g., tube or a roll-on applicator. In one embodiment, the composition is applied once or twice per day.

The compositions can be used to improve the shininess or glossiness) of a tooth surface. A glossmeter can be used to assess the shine or gloss of a surface.

EXAMPLES

The invention will now be illustrated by means of examples. The following tooth gloss measurement method was used in the examples.

1. Screen samples for matching baseline color for each study using a spectrophotometer. The delta E between teeth must be <2.3 units.
2. Etch selected teeth using a 1% citric acid solution for 6 minutes.
3. Take the baseline gloss measurement of the sample using a calibrated gloss meter (the baseline gloss reading for the acid treated teeth must be less than 15 gloss units).
4. Apply product evenly on the surface of the samples.
5. Allow samples to air dry.
6. Evaluate teeth for gloss using, a Novo Curve gloss meter Example 1

The following formulae were prepared and evaluated on bovine enamel:

TABLE 1

| Material | % |
|---|---|
| Anhydrous ethyl alcohol | 30 |
| Polymethylsilsesquioxane (Belsil PMS MK) | 70 |

TABLE 2

| Material | % |
|---|---|
| Anhydrous ethyl alcohol | 80 |
| Shellac | 20 |

Bovine teeth were treated with a paint-on formula containing either polymethylsilsesquioxane resin (Table 1) or shellac (Table 2) and evaluated using a gloss meter. Six teeth were treated, and the results were averaged. The results are shown in Table 3 below. The formula comprising silicone resin provided the greatest change in enamel shine demonstrating that such compositions provide better glossing results than shellac-containing compositions.

TABLE 3

| Tooth | Shellac | | | Polymethylsilsesquioxane | | |
|---|---|---|---|---|---|---|
| | Baseline | After | Delta | Baseline | After | Delta |
| 1 | 16.5 | 27.5 | 11 | 24.5 | 48.1 | 23.6 |
| 2 | 35.2 | 41.3 | 6.1 | 20 | 44 | 24 |
| 3 | 17.7 | 25.1 | 7.4 | 15.3 | 38.4 | 23.1 |
| 4 | 20.1 | 31.2 | 11.1 | 24.2 | 39.2 | 15 |
| 5 | 22.4 | 31.3 | 8.9 | 25.3 | 44 | 18.7 |
| 6 | 19.4 | 31.3 | 11.9 | 22.5 | 41.7 | 19.2 |
| Average | 21.9 | 31.3 | 9.4 | 21.9 | 42.6 | 20.7 |

Example 2

An employee visual evaluation of shine on bovine samples coated with different film forming formulae was conducted. Test formulae, shown below, were applied evenly on bovine enamel and air dried. Samples were then blinded in preparation for the visual test.

TABLE 4

At above 20% in the formula, shellac and TMS could not mix homogeneously in a reasonable amount of time.

| Material | Sample A % | Sample B % | Sample C % |
|---|---|---|---|
| Anhydrous ethyl alcohol | 80 | 80 | 30 |
| Polymethylsilsesquioxane | — | — | 70 |
| Shellac | 20 | — | — |
| Trimethylsiloxysilicate (TMS 803) | — | 20 | — |
| Total | 100 | 100 | 100 |

From the results obtained, Sample C containing polymethylsilsesquioxane provided the best enamel shine as identified by the panelists.

TABLE 5

| | Sample A | Sample B | Sample C |
|---|---|---|---|
| Shiniest | — | — | 10 |
| Least Shiniest | 1 | 9 | — |

The increase in shine provided by each resin coating was also quantified using a glossmeter. In the in vitro experiment, bovine enamel was treated with all three formulae from Table 4. The data as analysed using the Tukey method a shown below in Table 6. The results matched the employee visual evaluation results. Means that do not share a letter are significantly different

TABLE 6

| C1 | N | Mean | Grouping |
|---|---|---|---|
| polymethylsilsesquioxane | 6 | 20.617 | A |
| Shellac | 6 | 9.415 | B |
| Trimethylsiloxysilicate | 6 | −2.392 | C |

The data demonstrates that polymethylsilsesquioxane resin offers visibly shinier enamel surface as compared to shellac and trimethylsiloxysilicate resin. It is impressive that a formula containing a silicone resin (polymethylsilsesquioxane) can provide greater gloss than shellac. It is unexpected that polymethylsilsesquioxane (in which each silicon atom is attached to three oxygen atoms and one R group) would provide significantly better shine than other silicone resins such as trimethylsiloxysilicate (in which every silicon atom is attached to four oxygen atoms).

We claim:

1. An oral care composition comprising
    (i) a silsesquioxane silicone resin and
    (ii) a solvent,
wherein the composition comprises from 60 to 80 weight % silsesquioxane silicone resin.

2. The oral care composition according to claim 1 wherein the silicone resin comprises at least 50 mole % trifunctional units of formula $RSiO_{3/2}$ wherein R is the same or different and is selected from hydrogen, $C_1$ to $C_4$ alkyl, aryl and phenyl.

3. The oral care composition according to claim 1 wherein the silicone resin comprises from 50 mole % to 100 mole % trifunctional units of formula $RSiO_{3/2}$ wherein R is the same or different and is selected from hydrogen, $C_1$ to $C_4$ alkyl, aryl and phenyl.

4. The oral care composition according to claim 1 wherein the silicone resin comprises from 60 mole % to 99 mole % trifunctional units of formula $RSiO_{3/2}$ wherein R is the same or different and is selected from hydrogen, $C_1$ to $C_4$ alkyl, aryl and phenyl.

5. The oral care composition according to claim 2 wherein from 60 mole % to 100 mole % R is methyl.

6. The oral care composition of claim 1 wherein the silsesquioxane silicone resin is polymethylsilsesquioxane.

7. The oral care composition according to claim 1 wherein the solvent comprises one or more of ethanol, ethyl acetate, and mixtures thereof.

8. The oral care composition according to claim 1 wherein the solvent comprises ethanol.

9. The oral care composition according to claim 1 wherein the solvent consists of ethanol.

10. The oral care composition according to claim 1 wherein the composition comprises from 65 to 75 weight % silsesquioxane silicone resin.

11. The oral care composition according to claim 1 wherein the composition comprises 70 weight % silsesquioxane silicone resin.

12. The oral care composition according to claim 1 wherein the composition comprises 10 to 40 weight % solvent.

13. The oral care composition according to claim 1 wherein the composition comprises 20 to 40 weight % solvent.

14. The oral care composition according to claim 1 wherein the composition comprises 40 weight % solvent.

15. The oral care composition according to claim 1 wherein the composition comprises 60 to 80 weight % silsesquioxane silicone resin and 20 to 40 weight % solvent.

16. The oral care composition according to claim 1 wherein the composition comprises 70 weight % silsesquioxane silicone resin and 30 weight % solvent.

17. The oral care composition according to claim 1 wherein the composition comprises less than 5 weight % water.

18. The oral care composition according to claim 1 wherein the composition comprises less than 1 weight % water.

19. The oral care composition according to claim 1 wherein the composition comprises from 0 to 1 weight % water.

20. The oral care composition according to claim 1 wherein the oral care composition is a paint-on composition, tooth varnish, sealant or coating.

21. The oral care composition according to claim 1 wherein the oral care composition further comprises an oral care active selected from one or more of a fluoride ion source, an antisensitivity agent, a tooth whitening agent, a tooth bleaching agent, an antibacterial agent, an anti-calculus agent and mixtures thereof.

22. The oral care composition according to claim 1 wherein the oral care composition further comprises a flavour agent.

23. A method of treating a tooth comprising applying a composition according to claim 1 to a surface of a tooth.

24. A method of tooth glossing comprising applying a composition according to claim 1 to a surface of a tooth.

\* \* \* \* \*